United States Patent [19]

Thomas

[11] 4,094,664

[45] June 13, 1978

[54] PLANT GROWTH REGULATING AGENTS

[75] Inventor: Gareth John Thomas, Hitchin, England

[73] Assignee: Hoffmann-La Roche Inc., Nutley, N.J.

[21] Appl. No.: 655,301

[22] Filed: Feb. 4, 1976

[51] Int. Cl.$^2$ .............................................. A01N 9/24
[52] U.S. Cl. ........................................ 71/115; 71/70; 71/76; 71/78; 71/88; 71/89; 71/103
[58] Field of Search ...................... 71/115, 76, DIG. 1

[56] References Cited

U.S. PATENT DOCUMENTS

| | | | |
|---|---|---|---|
| 2,840,595 | 6/1958 | Stevens | 71/76 |
| 3,014,063 | 12/1961 | McLane et al. | 71/115 |
| 3,671,215 | 6/1972 | Beilsmith et al. | 71/115 |
| 3,736,112 | 5/1973 | Abramitis et al. | 71/DIG. 1 |
| 3,737,551 | 6/1973 | Karsten et al. | 71/DIG. 1 |
| 3,778,248 | 12/1973 | Weston et al. | 71/115 |
| 3,948,636 | 4/1976 | Marks | 71/DIG. 1 |

OTHER PUBLICATIONS

James et al., "Plant Growth-Regulating Substances," (1968), CA69, No. 26178p, (1968).
Widholm I, "Tryptophan Biosynthesis in N. Tabacum etc.," (1971), Biochim. & Biophys. Acta 261 pp. 44–51 (1972).
Widholm II, "Cultured N. Tabacum Cells etc.," (1971), Biochim. & Biophys. Acta 261, pp. 52–58 (1972).
James et al., "Studies on Plant Growth-Regulating, etc.," (1967), J. App. Biol. 61, pp. 295–302 (1968).

*Primary Examiner*—Glennon H. Hollrah
*Attorney, Agent, or Firm*—Samuel L. Welt; Bernard S. Leon; William M. Farley

[57] ABSTRACT

Plant growth regulating and herbicidal compositions, and methods for their use, containing as the active ingredient 6-amino-o-toluic acid or agriculturally acceptable salts thereof.

4 Claims, No Drawings

PLANT GROWTH REGULATING AGENTS

BRIEF SUMMARY OF THE INVENTION

This invention relates to plant growth regulating and herbicidal compositions, as well as methods for controlling plant growth, utilizing as the active ingredient 6-amino-o-toluic acid or agriculturally acceptable salts thereof.

DETAILED DESCRIPTION OF THE INVENTION

The compositions and methods of this invention, containing 6-amino-o-toluic acid or agriculturally acceptable salts thereof as the active ingredient, are useful becasue of both their pre-emergent and post-emergent plant growth regulant activity and herbicidal activity. However, the post-emergent plant growth regulating activity is most significant.

As used herein, "plant growth regulant" means a compound or composition which affects the maturation and metabolism of plants. Hence, a "plant growth regulant" has many effects on plant growth. However, not all plant growth regulant active compounds and compositions affect plants the same way. For example, plant growth regulants could affect vegetative growth by retarding or stimulating terminal growth, and/or stimulating side branching and could inhibit new growth such as the development of new sprouts of woody plants, the sprouting of tubers and rhizomes and the development of sucker growth. Such regulants could affect flowering plants by eliminating early flowering, by thinning of blossoms or by increasing the number of flowers. Fruit-bearing trees and bushes could be affected by increases in the number, size and quality of the fruit, by parthenocarpy, by producing seedless fruit, by accelerating senescence and fruit ripening and by influencing the abscission of fruit. Both flowering and fruit plants could be affected by accelerating plant dormancy and maintaining bud dormancy. A "plant growth regulant" could cause selective post-emergent control of weeds by reducing their vigor and competitiveness and, thus, prevent their spread and stop normal seeding. In addition, such compounds and compositions have an influence on the transport of substances within plants; e.g., they stimulate latex flow and/or metabolism or increase the sugar content within the plant, which may also increase frost resistance. Such compounds or compositions may affect the extent of stomatal opening and thus increase drought resistance and reduce or even eliminate harmful effects of atmospheric pollutants (e.g. ozone and sulfur dioxide).

Specifically, compositions containing the active ingredient of this invention, i.e., 6-amino-o-toluic acid or an agriculturally acceptable salt thereof, are especially active in stimulating latex flow.

The expression "intact plant" as used herein denotes a normal growing plant as opposed to a detached part of a plant, e.g., stem segments, coleoptiles or any other explant.

The plant growth regulating compositions of this invention are especially active in regulating the growth of the following plants and, in particular, young plants:
(a) Cereals such as corn, wheat, rye, barley, oats, etc.;
(b) Trees and shrubs such as fruit trees (e.g., apple, pear, peach, cherry and lemon) as well as cocoa, tea, coffee, banana, rubber, olive and walnut;
(c) Ornamental plants such as privet, hornbeam, white cedar, juniper, rose, azalea, chrysanthemum, poinsettia, cyclamen, pyrocantha, forsythia, magnolia, petunia and bromeliad;
(d) Field plants such as, for example, grapevine, cotton, soya bean, groundnut, tobacco, flax, sugar beet and pineapple;
(e) Vegetables such as Solanaceae (e.g., tomatoes), legumes, pumpkins, melons etc.;
(f) Berries such as strawberries, bilberries, raspberries, blueberries, blackberries and red currants and
(g) Grasses.

"Plant growth regulant" also means the retardation of terminal (i.e., vertical) growth of plants. In grasses and weeds, this regulant activity will retard the grass height and, hence, grass growth. In bush plants and shrubs, on the other hand, the resultant retardation of terminal growth by the regulant activity often results in enhancement of lateral or side growth, an effect desired, e.g., in tomato plants.

In order to effect uniform distribution of the active ingredient, 6-amino-o-toluic acid or an agriculturally acceptable salt thereof, of the growth regulating and herbididal compositions according to this invention, the compound can be mixed with liquid or solid agriculturally acceptable adjuvants conventionally used for such applications so that they may be formulated as solutions, emulsions, emulsifiable concentrates, dispersions, dusts, granulates or wettable powders.

The term "agriculturally acceptable adjuvant" as used herein includes:
(a) agriculturally acceptable inert carrier materials as, for example, surface active agents, carriers, sticking agents, stabilizers, filler, modifiers, diluents, conditioning agents and the like and
(b) other active agricultural materials such as herbicides, fungicides, insecticides, or plant growth regulants which complement the active plant growth regulant ingredient or extend the useful life of the composition.

It is understood, of course, that the adjuvant added to the plant growth regulant compositions of this invention comprises either only the inert materials of (a), the active materials of (b) or a combination of materials from (a) and (b).

Liquid formulations of 6-amino-o-toluic acid for direct spraying may be made, for example, as aqueous solutions of agriculturally acceptable salts where possible or as solutions in solvent mixtures as, for example, an acetone/water mixture.

Emulsifiable concentrates can be prepared containing 5–50% or more of 6-amino-o-toluic acid depending on the solubility thereof using suitable solvents such as N-methyl-pyrrolidine, dimethylformamide, cyclohexanone, etc. Surface-active substances (e.g., wetting agents, dispersants, emulsifiers and the like) are added in sufficient amounts to impart the desired characteristics to the formulations.

6-Amino-o-toluic acid or agriculturally acceptable salts thereof can be prepared in the following forms or pre-mixes for use as a plant growth regulant and/or herbicide. The concentration of active ingredient refers to the acid form.

(a) as an aqueous concentrate containing from about 10% to about 50% by weight of the active ingredient;

(b) as a ready-to-use solution containing from about 0.0001% to about 10% by weight of the active ingredient;

(c) as a water-soluble powder containing from about 10% to about 90% by weight of the active ingredient;

(d) as a sprayable powder containing from about 35% to about 65% by weight of the active ingredient;

(e) as a dusting powder or granule containing from about 2% to about 10% by weight of the active ingredient and (f) as a flowable liquid containing from about 10% to about 40% by weight of the active ingredient.

Different forms of application may be better adapted to the various purposes for which 6-amino-o-toluic acid is to be used by the addition of substances which improve dispersion, adhesion, resistance to rain and penetrative powder such as fatty acids, waxes, resins, wetting agents, emulsifying agents, mineral oils, vegetable oils, binding agents and the like. In a similar manner, the biological spectrum may be broadened by the addition of substances having bactericidal, herbicidal, and fungicidal properties and also by combination with fertilizers, chelating agents and other plant growth regulators.

Representative of herbicides and plant growth regulants which may be admixed with 6-amino-o-toluic acid in plant growth regulating and herbicidal compositions of this invention are:
2,2-dichloropropionic acid,
N-(4-aminobenzenesulphonyl)methylcarbamate,
2-chloro-4-ethylamino-6-isopropylamino-1,3,5-triazine,
4-chloro-2-oxobenzothiazolin-3-yl-acetic acid,
5-bromo-6-methyl-3-(1-methyl-n-propyl)uracil,
3,5-dibromo-4-hydroxybenzonitrile,
D,N-ethyl-2-(phenylcarbamoyloxy) propionamide,
N-(4-bromo-3-chlorophenyl)-N'-methoxy-N'-methylurea,
methyl 2-chloro-9-hydroxyfluorene-9-carboxylate,
N'-4-(4-chlorophenoxy)-phenyl-N,N-dimethylurea,
isopropyl-N-(3-chlorophenyl)-carbamate,
2,3,5,6-tetrachloroterephthalic acid dimethyl ester (DCPA),
2,4-dichlorophenoxyacetic acid,
4-isopropylamino-6-methylamino-2-methylthio-1,3,5-triazine,
n-butyl 9-hydroxyfluorene-9-carboxylate,
ethylene,
naphthoxyacetic acid,
3,6-dichloro-2-methoxybenzoic acid,
(±)-2-(2,4-dichlorophenoxy)propionic acid,
9,10-dihydro-8a,10a-diazoniaphenanthrene-2A,
N'-(3,4-dichlorophenyl)-N,N-dimethylurea,
gibberellic acid,
indolylacetic acid,
indolylbutyric acid,
4-hydroxy-3,5-diiodobenzonitrile,
N'-(3,4-dichlorophenyl)-N-methoxy-N-methylurea,
(4-chloro-2-methylphenoxy)acetic acid,
4-(4-chloro-2-methylphenoxy)butyric acid,
(±)-2-(4-chloro-2-methylphenoxy)propionic acid,
N-(benzothiazol-2-yl)-N,N'-dimethylurea,
N'-(3-chloro-4-methoxyphenyl)-N,N-dimethylurea,
1,2,3,6-tetrahydro-3,6-dioxopyridiazine,
N'-(4-chlorophenyl)-N-methoxy-N-methylurea,
N'-(4-chlorophenyl)-N,N-dimethylurea,
naphthylacetic acid,
N-1-naphthylphthalamic acid,
2,4-dichlorophenyl 4-nitrophenyl ether,
1,1'-dimethyl-4,4'-bipyridylium-2A,
3-(m-tolylcarbamoyloxy)phenyl carbamate,
4-amino-3,5,6-trichloropicolinic acid,
4,6-bis-isopropylamino-2-methylthio-1,3,5-triazine,
N-(3,4-dichlorophenyl)-propionamide,
isopropyl-N-phenylcarbamate,
5-amino-4-chloro-2-phenylpyridazin-3(2H)-one,
N-dimethylaminosuccinic acid,
2-chloroethylphosphorus acid,
tributyl-2,4-dichlorobenzyl-phosphonium chloride,
2,4,5-trichlorphenoxypropionic acid,
2,3,6-trichlorobenzoic acid,
2-chloro-4,6-bis-ethylamino-1,3,5-triazine,
sodium chloroacetate,
2,4,5-trichlorophenoxyacetic acid,
5-chloro-6-methyl-3-tert.butyluracil,
4-ethylamino-2-methylthio-6-tert. butylamino-1,3,5-triazine-(tert.Butyryn),
2,3,5-triiodobenzoic acid and
1,1,4-trimethyl-6-isopropyl-5-propionyl-indane.

Examples of fungicides which may be admixed with 6-amino-o-toluic acid in the plant growth regulating compositions of this invention are:
2,4-dichloro-6-(o-chloraniline)-S-triazine,
2,4,5,6-tetrachloroisophthalic acid nitrile,
p-dimethylaminophenyldiazo sodium sulphonate,
1,4-dichloro-2,5-dimethoxybenzene,
manganese ethylene-bis-dithiocarbamate,
zinc ethylene-bis-dithiocarbamate,
coordination product from zinc and manganese ethylene-bis-dithiocarbamate,
methyl 1-(butylcarbamoyl)-2-benzimidazole carbamate,
2-(4-thiazole)-benzimidazole and
cis-N-[(trichloromethyl)-thio]-4-cyclohexene-1,2-dicarboximide.

Rates of application are based upon the results reported herein and are not to be deemed all--inclusive since many extraneous factors can alter the rates of application. For example, rates may vary not only among different plant species but also within a particular species depending on such factors as plant size and age, the compound used, the time of year, type of soil and such climatological conditions at application time as air temperature, light intensity, rainfall and winds. In addition, if 6-amino-o-toluic acid or a plant growth regulating composition containing 6-amino-o-toluic acid or an agriculturally acceptable salt thereof as the active ingredient is applied via a soil drench, higher concentrations would be needed since this type of application is indirect in comparison to a direct application upon the leaves and stems, e.g. spraying.

The amount of active ingredient in the growth regulating or herbicidal compositions of this invention thus varies according to the plants to be controlled, the requisite application rate, type of application and the control desired. Generally, the plant growth regulating and herbicidal compositions of this invention contain less than 50% of 6-amino-o-toluic acid when in a ready-to-use spray formulation, from about 35% to about 65% of the active ingredient when in a sprayable powder form and form about 0.0001% to about 10% of the active ingredient when in a ready-to-use solvent.

Basically, the application rate of 6-amino-o-toluic acid is that which is effective in providing the requisite growth regulant control to the plant.

Hence, the choice of the minimum application rate would be determined by the minimum amount of 6- amino-o-toluic acid which is effective in regulating growth to the lowest limit of the desired growth retardation range. The choice of the maximum application rate would be determined as that amount which is effective in regulating growth to the upper limit of the desired growth retardation range. In the control of grasses, particularly home lawns and industrial turfs, e.g. golf courses, it has been established that a maximum growth retardation as evidenced by diminished grass height as compared to an untreated control of about 40%–60% is desirable with about 50% growth retardation preferred. Any retardation less than 40% is ineffective in that grass control is not substantial enough to have a significant aesthetic effect and to reduce or eliminate manual care. On the other hand, retardation greater than 60% results in an undesired skimpy appearance to the lawn or turf with subsequent invasion thereof by weeds and other undesired plants.

With tomato plants, the criteria for an effective growth retardation activity are rates such as would provide a dwarfed, bushy plant with no loss of fruit quality or quantity. The parameters for effective growth regulant activity for such plants are retarded terminal growth and enhanced or non-retarded lateral growth as the minimum effects and retarded terminal and lateral growth as the maximum effects. Application rates of 6-amino-o-toluic acid which have these desired effects on tomato plant growth are determined with these criteria in mind. In order to obtain the greatest post-emergent growth regulating activity, application rates of from about 0.5 kg. to about 10 kg. or more of 6-amino-o-toluic acid per hectare generally are needed. The greatest post-emergence growth regulating activity is normally obtained with application rates of from about 1 to 5 kg. or more of 6-amino-o-toluic acid per hectare. A preferred dosage range in solutions for spray application is from about 1 to 150,000 ppm or more depending on the species to be treated. The most preferred range for spray application is from about 100 to 10,000 ppm.

An additional advantage in the use of 6-amino-o-toluic acid and its agriculturally acceptable salts and the plant growth regulating and herbicidal compositions of this invention is the absence of any permanent effect on plants or any regulant residue in the soil. 6-Amino-o-toluic acid undergoes slow decomposition and, thus, there is a consequent diminution of activity. Such an effect is advantageous in that (a) a short-term effect, which can be lengthened by subsequent additional application, is attained;
(b) normal growth activity resumes as the regulant activity decreases; and
(c) no deleterious residues remain on the plants or in the soil.

The length of the retardant effect varies with such factors as the plant species, climatological conditions and the like.

Although exhibiting plant growth regulant activity, 6-amino-o-toluic acid is virtually non-toxic to animals.

6-Amino-o-toluic acid functions as a herbicide when applied, as described above, to weeds including *Digitaria sanguinalis, Rumex obtusifolius, Sorghum halepense, Imperata cylindrica,* Parricum spp. and Paspalurn spp.

One advantage of this invention is that it provides plant growth regulating compositions containing 6-amino-o-toluic acid or an agriculturally acceptable salt thereof which exhibit pre-emergent and post-emergent growth regulating activity when applied to various plants and/or herbicidal activity. This effect is noted on a wide spectrum of plants.

Representative compositions containing 6-amino-o-toluic acid and suitable for use, as described herein, as plant growth regulants and/or herbicides are set forth below.

A. Aqueous Compositions

6-Amino-o-toluic acid is amphoteric in nature and, thus, can form water-soluble agriculturally acceptable salts with either acids or bases. By the term "agriculturally acceptable salts" is meant those salts of 6-amino-o-toluic acid, formed from acids or bases, which do not interfere with the plant growth regulant or herbicidal activity of 6-amino-o-toluic acid and which do not have a deleterious effect on the plants or grasses to which applied. Representative acids and bases which form such agriculturally acceptable salts are listed below.

(a) Aqueous Compositions with Bases

A representative composition if formed by admixing the following ingredients:

|   | A |
|---|---|
| 6-amino-o-toluic acid | 200 grams |
| Diethanolamine | 150 grams |
| Deionized water | to 1000 ml. |

While other bases can be used in these compositions, a limiting factor is the water-solubility of the resulting salt since the concentration of the active ingredient in these aqueous compositions is dependent on salt solubility. Representative bases include dimethylamine, triethanolamine, aminomethylpropanol and morpholine.

To improve the wetting action of these aqueous systems, the compositions can also contain from about 0.01% to about 0.05% of an anionic or non-ionic surfactant. Representative anionic surfactants include an alkali metal salt of an alkyl sulfate (e.g., sodium lauryl sulfate) or an alkali metal salt of an alkyl arylsulfonic acid (e.g., sodium dodecyl benzenesulfonate). Representative non-ionic surfactants include condensation products of ethylene oxide with alkyl phenols (e.g., the condensation product of nonyl-phenol with 8 to 10 moles of ethylene oxide) and condensation products of ethylene oxide with fatty alcohols (e.g., the condensation product of stearyl alcohol with 8 to 10 moles of ethylene oxide).

Typical compositions containing a surfactant are formed by admixture of the following ingredients.

|   | B | C |
|---|---|---|
| 6-amino-o-toluic acid | 200 g. | 200 g. |
| Surfactant | 6.25 g. | 100 g. |
| Diethanolamine | 150 g. | 150 g. |
| Deionized water | to 1000 ml. | to 1000 ml. |

Compositions B and C above can be diluted prior to use to solutions containing 0.8% and 0.05% of active ingredient respectively and 0.025% surfactant. Since these compositions are diluted prior to use to yield a concentration of active ingredient in the range of from about 0.01% to about 1.0%, the concentration of surfactant must be adjusted to provide a final concentration of from about 0.01% to about 0.05%.

(b) Aqueous Compositions with Acids

Representative compositions are prepared by admixing the following ingredients:

|  | D | E | F |
|---|---|---|---|
| 6-amino-o-toluic acid | 100g. | 100g. | 100g. |
| Hydrochloric acid (32%) | 151g. | 151g. | 151g. |
| Surfactant | — | 6.25g. | 100 g. |
| Deionized water | to 1000ml. | to 1000ml. | to 1000ml. |

Acids such as hydrochloric, sulfuric, phosphoric and acetic form suitable salts with 6-amino-o-toluic acid. Hydrochloric acid is preferred since the resulting salt is the most soluble.

The surfactant used in these acid-based formulations can be either non-ionic or cationic. Non-ionic surfactants were discussed above. Representative cationic surfactants include the alkylbenzylammonium compounds such as dodecyldimethylbenzylammonium chloride.

Compositions E and F above can be diluted prior to use to solutions containing 0.8% and 0.05% of active ingredient respectively and 0.025% of the surfactant.

Since these compositions are also diluted prior to use to yield a concentration of active ingredient within the range of from about 0.01% to about 1%, the concentration of surfactant must be adjusted to provide a final concentration within the range of about 0.01% to about 0.05%.

B. Water-soluble Powder Compositions

The following representative compositions are prepared by admixing and finely milling the ingredients to form free-flowing powders which are water-wettable and dissolve to form clear solutions:

|  | G | H |
|---|---|---|
| 6-amino-o-toluic acid | 20g. | 20g. |
| Soda, calcined | 15.5g. | — |
| Lactose | 63.5g. | 66.0g. |
| Sulfaminic acid | — | 13.0g. |
| Surfactant, anionic | 1.0 | — |
| Surfactant, non-ionic | — | 1.0 |

For Composition G, the anionic surfactant was sodium lauryl sulfate. For Composition H, the non-ionic surfactant was an ethylene oxide-propylene oxide solid block polymerisate containing 80% polyethylene glycol ether chains.

C. Solid Compositions

(a) Spray Powder (Wettable Powder)

The following ingredients are admixed and finely milled to yield free-flowing powders which are water-wettable and form a stable suspension.

|  | H |
|---|---|
| 6-amino-o-toluic acid | 50.0g. |
| Silicic acid, hydrated | 5.0g. |
| Sodium lauryl sulfate | 1.0g. |
| Sodium ligno-sulfonate | 2.0g. |
| Kaolin | 42.0g. |

Sodium lignosulfonate functions as a dispersant.

(b) Dusting Agent

The following ingredients are mixed and milled to form a powder having good dusting capability:

|  | H |
|---|---|
| 6-amino-o-toluic acid | 5.0g. |
| Talc | 95.0g. |

(c) Granulate

The following ingredients are used to form the granulate:

|  | I |
|---|---|
| 6-amino-0-toluic acid | 5.0g. |
| Polyethylene glycol (PEG 500) | 2.0g. |
| Calcium carbonate | 93.0g. |

Calcium carbonate granules, 1 mm. in diameter, are uniformly sprayed with the polyethylene glycol. This mixture is then admixed with finely milled 6-amino-o-toluic acid. The polyethylene glycol acts as an adhesive to bind the active ingredient to the calcium carbonate carrier particles.

D. Miscellaneous Compositions

(a) Spray Dispersion Composition

The following components are mixed and ball milled until the particle size of 6-amino-o-toluic acid is within the range of about 1 to about 5 microns:

|  | I |
|---|---|
| 6-amino-o-toluic acid | 250g. |
| Sodium salt of a sulfonated naphthalene-formaldehyde condensation product (dispersent) | 25g. |
| Bentonite | 15g. |
| Deionized water | to 1000 ml. |

The resulting preparation is a homogeneous, free-pouring composition which is dispersible in water to form a ready-to-use spray dispersion.

(b) Emulsifiable concentrate

The following ingredients comprise an emulsion concentrate

|  | J |
|---|---|
| 6-amino-o-toluic acid | 100g. |
| Emulsifier | 100g. |
| Cyclohexanone | to 1000 ml. |

The 6-amino-o-toluic acid and the emulsifier are dissolved in cyclohexanone to form a clear solution. This concentrate when added to water emulsifies immediately.

A preferred emulsifier is a mixture of a condensation product of nonyl phenol with 8–10 moles of ethylene oxide and the calcium salt of dodecylbenzene sulfonic acid.

(c) Spray Solution

The following ingredients are admixed

|  | K |
| --- | --- |
| 6-amino-o-toluic acid | 2.0g. |
| Tensiofix AS Surfactant | 0.1g. |
| Acetone | 97.9g. |

For use, this solution is usually diluted, just prior to application, with water and Tween 20 to give a final concentration of from about 0.1% to about 0.2% by weight of 6-amino-o-toluic acid.

Tensiofix AS is a mixture of nonionic alkylphenol derivatives, polyethylene oxide alkylphenol condensation product and anionic dodecyl benzene sulfonate containing small amounts of n-butanol and carbon tetrachloride.

Tween 20 is a polyoxyalkylene derivative of sorbitan monolaurate.

6-Amino-o-toluic acid is a known compound and its preparatory procedure is described in Ber: 1919, 52, 1079.

o-Toluic acid (2-methylbenzoic acid) is prepared from the partial oxidation of o-xylene and the 6-amino-o-toluic acid can be prepared, e.g., by the catalytic hydrogenation of 2-methyl-6-nitrobenzoic acid.

Furthermore, in Ann. Appl. Biol. (1968), 61, 295-302, 6-amino-o-toluic acid was evaluated as a plant growth regulant and disclosed as inactive for such use.

The following examples illustrate the invention.

EXAMPLE 1

Solutions, suitable for spraying, were prepared in the concentrations listed below. All concentrations are reported in percents by weight based on the total weight of the solutions.

|  |  | Concentration | | |
| --- | --- | --- | --- | --- |
| Ingredient | Solution- | A | B | C |
| 6-amino-o-toluic acid |  | 1.0 | 0.5 | 0.25 |
| Tensiofix AS |  | 0.1 | 0.1 | 0.1 |
| Acetone |  | 48.9 | 49.4 | 49.65 |
| Water |  | 50.0 | 50.0 | 50.0 |

Each solution was applied, by spraying until run-off, at application rates of from 2.5 to 10 kg/hectare, to each of the following plants:
*Soghum halepense* (Johnson grass)
*Rumex obtusifolius* (Broad-leaf dock)
*Chrysanthemum segetum*
*Panicum miliareum* (Proso millet)

Plant response, i.e., necrosis, was evaluated three weeks after spraying by determining the area of necrosis on the plant leaves. Test results are given in Table I below.

Table I

| Test Plant | (kg/ha.) | % of Leaf Area Necrotic | | |
| --- | --- | --- | --- | --- |
|  |  | 2.5 | 5.0 | 10.0 |
| Sorghum halepense |  | 80 | 90 | 100 |
| Rumex obtusifolius |  | 80 | 100 | 100 |
| Chrysanthemum segetum |  | 100 | 100 | 100 |
| Panicum miliaceum |  | 90 | 100 | 80 |

EXAMPLE 2

This Example demonstrates the growth retarding activity of 6-amino-o-toluic acid on wheat, barley and blue grass.

A spray solution containing, in percents by weight based on the weight of the composition, 0.4% 6-amino-o-toluic acid, 49.5% acetone, 0.1% Tensiofix AS and 50% water was prepared. Test plants were sprayed with this solution until run-off, i.e. an application rate of 4 kg./hectare. The results, listed in Table II below, are reported as % growth retardation relative to untreated controls.

Table II.

| Test Plants | % Growth retardation |
| --- | --- |
| wheat (*triticum aestivum*) | 25 |
| barley (*Hordeium distichon*) | 40 |
| blue grass (*Poa pratensis*) | 75 |

EXAMPLE 3

This Example compares the growth retarding activity of 6-amino-o-toluic acid with that of a known plant growth regulator--2-chloroethyl trimethyl chloride (CCC) on wheat (*Triticum asetivum* "Svenna") and barley (*Hordeum distichon* "Union") plants.

2% Solutions of each active ingredient were prepared using acetone/water as the solvent with 0.2% Tween 20 as surfactant.

The test plants, divided into groups with six plants in each group, were treated with the above solutions at the rate of 1000 ppm of active ingredient for CCC and 1000, 500 and 250 ppm of active ingredient for 6-amino-o-toluic acid. All treated plants were kept in a greenhouse, maintained at a mean relative humidity of 70% with an average night temperature of 18° C. and an average day temperature of 22°-26° C., during the entire test period.

The plants were treated initially at their 3-leaf growth stage and again at their 6-leaf growth stage.

Three weeks after each application the plants in each group were measured. The results, presented below in Table III, show that 6-amino-o-toluic acid is superior as a plant growth regulant to CCC on both wheat and barley at 1000 ppm.

Table III

| Test Plant | Growth Stage/ppm | Average height, cm. | | | | |
| --- | --- | --- | --- | --- | --- | --- |
|  |  | Untreated | CCC | 6-amino-o-toluic acid | | |
|  |  | 0 | 1000 | 1000 | 500 | 250 |
| Wheat (*Triticum aestivum*) | 3 leaf | 15.9 | 9.9 | 5.6 | 7.2 | 12.1 |
| Wheat (*Triticum aestivum*) | 6 leaf | 21.0 | 19.2 | 16.2 | 23.5 | 25.8 |
| Barley (*Hordeum distichon*) | 3 leaf | 19.8 | 16.0 | 9.2 | 9.8 | 18.7 |
| Barley (*Hordeum distichon*) | 6 leaf | 33.4 | 26.5 | 14.3 | 25.3 | 29.8 |

EXAMPLE 4

This example compares the growth regulating activity of 6-amino-o-toluic acid with that of a known plant growth regulating agent "Sustar" [3'-trifluoromethylsulfonamide)-acetotluide] on the four grass species listed in Table IV below.

Solutions of each active ingredient were prepared as in Example 3 above using only 0.1% Tween 20 as surfactant.

The test plants, divided into groups of six plants each, were treated, when 4 cm. in height, with one of the above solutions at the rate of 2 and 4 kg. per hectare of active ingredient for "Sustar" and at the rate of 1, 0.5 and 0.25 kg. per hectare of active ingredient for 6-amino-o-toluic acid. All treated plants were kept in a greenhouse maintained at mean relative humidity of 70% with an average night temperature of 18° C. and average day temperature of 22°–26° C. during the entire test period.

Grass heights were measured 3 weeks after treatment. The average heights of each group is recorded in Table IV below. The percentage growth reduction relative to untreated grass is also reported in Table IV. These results show that 6-amino-o-toluic acid applied at the rate of 1 kg./ha is superior to "Sustar" applied at the rate of 2 kg./ha on all grass species tested.

Table IV

|  | Grass Height, Cm. | | | | | | % Growth Reduction | | | | | |
| --- | --- | --- | --- | --- | --- | --- | --- | --- | --- | --- | --- | --- |
|  | Untreated | "Sustar" | | 6-amino-o-toluic acid | | | Untreated | "Sustar" | | 6-amino-o-toluic acid | | |
| Test Plant/kg.a.i./ha | 0 | 4 | 2 | 1 | 0.5 | 0.25 | 0 | 4 | 2 | 1 | 0.5 | 0.25 |
| Poa prastensis | 25 | 14 | 18 | 5 | 5 | 5 | 0 | 44 | 28 | 80 | 80 | 80 |
| Lolium perenne | 28 | 20 | 26 | 21 | 26 | 27 | 0 | 29 | 7 | 25 | 7 | 4 |
| Agrostis tenuis | 21 | 6 | 7 | 5 | 9 | 13 | 0 | 71 | 67 | 76 | 57 | 38 |
| Festuca rubra | 20 | 10 | 16 | 5 | 5 | 11 | 0 | 50 | 20 | 75 | 75 | 45 |

EXAMPLE 5

This example evaluates the parthenocarpic activity of 6-amino-o-toluic acid as compared to gibberellic acid (GA$_3$) on the tomato species *Lycopersicum esculentum* ("Tiny Tim") using the same greenhouse conditions as described in Example 3 and 4.

For each active ingredient, 2% solutions were prepared in acetone/water with 0.2% Tween 20.

When the tomato plants reached the growth stage showing flowers and green fruit, 10 flower buds on each plant were clipped and 2 drops of one of the above solutions were applied to each bud using a micropipette. Fifty-nine days later, when the fruits matured, they were counted, opened and checked for seeds. The number of fully developed fruits for each group are listed in Table V below. Only those tomato plants treated with 6-amino-o-toluic acid developed fruit and all of the fruit were parthenocarpic (i.e., seedless).

Table V

| Active Ingredient | Application Rate, ppm | Number of Matured Fruit |
| --- | --- | --- |
| Gibberellic acid (GA$_3$) | 50 | 0 |
|  | 10 | 0 |
| 6-amino-o-toluic acid | 1000 | 8 |
|  | 100 | 9 |
|  | 10 | 7 |

Table V-continued

| Active Ingredient | Application Rate, ppm | Number of Matured Fruit |
| --- | --- | --- |
|  | 1 | 10 |
|  | 0 | 0 |

EXAMPLE 6

This example illustrates the activity of 6-amino-o-toluic acid in fruit ripening. Tomato plants ("Tiny Tim") were sprayed to run off with a 100 ppm solution of 6-amino-o-toluic acid when half the fruits on the first truss were red. Over the next 19 days, fruits were picked as they ripened. At the end of the 19 day period, 27.2% of all fruits had ripened on the plants treated with 6-amino-o-toluic acid as compared to 22.9% on the untreated control plants.

Since ripening is thought to be related to the presence of ethylene, other plant effects believed due to ethylene, e.g. latex stimulation, fruit abscission, defoliation on cotton and nursery stock plants, may be regulated by the use of 6-amino-o-toluic acid.

EXAMPLE 7

This example illustrates the post-emergence herbicidal activity of 6-amino-o-toluic acid. This effect was demonstrated on *Digitaria sanguinalis* by spraying at the 3 leaf stage and on *Rumex obstusifolius* by spraying at the 2 leaf stage. In both cases, an application rate of 3 kg. a.i./ha. was used with a total spray volume of 1000 l/ha.

The plants were examined 3 weeks after spraying. 70% of the *D.sanguinalis* was destroyed while the *R. obtusifolius* was totally destroyed.

I claim:

1. A method for regulating the growth of plants which comprises applying to the plants, as the active ingredient, an amount of 6-amino-o-toluic acid or an agriculturally acceptable salt thereof which is effective in regulating plant growth.

2. The method of claim 1 wherein the active ingredient is applied from a plant growth regulating composition comprising an agriculturally acceptable adjuvant and, as the active ingredient, an amount of 6-amino-o-toluic acid or an agriculturally acceptable salt thereof which is effective in regulating plant growth.

3. The method of claim 1 wherein the active ingredient is applied to the plants at the rate of from about 0.5 kg. to about 10 kg. of active ingredient per hectare.

4. The method of claim 1 wherein the active ingredient is applied from a spray solution containing the active ingredient in a concentration of from about 1 part per million to about 150,000 parts per million.

* * * * *